United States Patent
Kobayashi et al.

(10) Patent No.: US 8,735,522 B2
(45) Date of Patent: May 27, 2014

(54) GOLD-POLYMER NANOSTRUCTURE-IMMOBILIZED SCANDIUM CATALYST AND ITS USE

(75) Inventors: Shu Kobayashi, Tokyo (JP); Hiroyuki Miyamura, Saitama (JP)

(73) Assignee: Japan Science and Technology Agency, Saitama (JP)

( * ) Notice: Subject to any disclaimer, the term of this patent is extended or adjusted under 35 U.S.C. 154(b) by 0 days.

(21) Appl. No.: 13/580,312

(22) PCT Filed: Feb. 16, 2011

(86) PCT No.: PCT/JP2011/053199
§ 371 (c)(1),
(2), (4) Date: Nov. 19, 2012

(87) PCT Pub. No.: WO2011/111482
PCT Pub. Date: Sep. 15, 2011

(65) Prior Publication Data
US 2013/0059999 A1 Mar. 7, 2013

(30) Foreign Application Priority Data
Mar. 9, 2010 (JP) .................................. 2010-051987

(51) Int. Cl.
*C08F 12/30* (2006.01)
*C08K 3/10* (2006.01)

(52) U.S. Cl.
USPC .......................................... 526/289; 524/403

(58) Field of Classification Search
USPC ............................. 524/403; 526/289; 568/312
See application file for complete search history.

(56) References Cited

U.S. PATENT DOCUMENTS
2009/0143607 A1 6/2009 Kobayashi et al.

FOREIGN PATENT DOCUMENTS

| EP | 1 184 076 | 3/2002 |
|---|---|---|
| JP | 2005-254115 | 9/2005 |
| JP | 2007-237116 | 9/2007 |
| WO | WO2005/084802 | 9/2005 |
| WO | WO2005/085307 | 9/2005 |
| WO | WO2011/111482 | 9/2011 |

OTHER PUBLICATIONS

Machine translation of Kobayashi et al. (JP 2005-254115), which was provided by Applicant.*

(Continued)

*Primary Examiner* — Ling Choi
*Assistant Examiner* — Catherine S Branch
(74) *Attorney, Agent, or Firm* — Jenkins, Wilson, Taylor & Hunt, P.A.

(57) ABSTRACT

The present invention provides a Scandium catalyst that can be used in water or water-soluble organic solvent with no leaching of Scandium. Provided is a gold-polymer nanostructure-immobilized Scandium catalyst, which is formed by preparing, in liquid phase, a mixture comprising gold clusters with from 1 to 50 nm of diameter, disulfide monomer, sulfonic acid salt of disulfide and Lewis acid metal compound represented by $ScY_3$, wherein Y is $OSO_2CF_3$ etc., and polymerizing the mixture in the presence of a radical polymerization initiator, wherein the disulfide monomer is represented by the formula below:

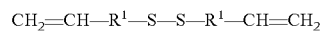

$$CH_2=CH-R^1-S-S-R^1-CH=CH_2$$

wherein $R^1$ represents a divalent hydrocarbon, which may contain an ether bond, and the sulfonic acid salt of disulfide is represented by the formula below:

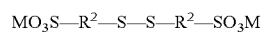

$$MO_3S-R^2-S-S-R^2-SO_3M$$

wherein $R^2$ represents a divalent hydrocarbon, which may contain an ether bond, and M represents an alkali metal. This catalyst is useful as a catalyst for aldol reactions, cyanolation reactions, allylation reactions, Michael reactions, Mannich reactions, Diels Alder reactions and Friedel Crafts reactions in water or water-soluble organic solvent.

6 Claims, 1 Drawing Sheet

(56) References Cited

OTHER PUBLICATIONS

Daniel et al., "Gold Nanoparticles: Assembly, Supramolecular Chemistry, Quantum-Size-Related Properties, and Applications toward Biology, Catalysis, and Nanotechnology," Chem. Rev. 2004, 104, 293-346.*

Balasubramanian et al., "Reaction of $Au_{55}(PPh_3)_{12}Cl_6$ with Thiols Yields Thiolate Monolayer Protected $Au_{75}$ Clusters," Journal of the American Chemical Society. vol. 127, No. 22 pp. 8126-8132 (2005).

International Search Report corresponding to International Patent Application No. PCT/JP2011/053199 dated May 31, 2011.

Notification Concerning Transmittal of International Preliminary Report on Patentability (Chapter I of the Patent Cooperation Treaty) corresponding to International Patent Application No. PCT/JP2011/053199 dated Sep. 20, 2012.

Shichibu et al., "Large-Scale Synthesis of Thiolated $Au_{25}$ Clusters via Ligand Exchange Reactions of Phosphine-Stabilized $Au_{11}$ Clusters," Journal of the American Chemical Society. vol. 127, No. 39 pp. 13464-13465 (2005).

Takeuchi et al., "Polymer-Micelle Incarcerated Scandium as a Polymer-Supported Catalyst for High-Throughput Organic Synthesis," Journal of the American Chemical Society. vol. 127, No. 38 pp. 13096-13097 (2005).

Woehrle et al., "Ligand Exchange Reactions Yield Subnanometer, Thiol-Stabilized Gold Particles with Defined Optical Transitions," The Journal of Physical Chemistry B. vol. 106, No. 39 pp. 9979-9981 (2002).

Supplementary European Search Report corresponding to European Patent Application No. 11 753 144.2-1352/2545991 dated Oct. 22, 2013.

\* cited by examiner

GOLD-POLYMER NANOSTRUCTURE-IMMOBILIZED SCANDIUM CATALYST AND ITS USE

FIELD OF THE INVENTION

The present invention relates to a polymer immobilized Scandium catalyst that can be used in water or a water-soluble organic solvent and has no leaching of Scandium, and a method for organic synthesis using said catalyst.

BACKGROUND OF THE INVENTION

Attempts have been made for many years to use metal polymer composite materials immobilizing various catalysts on a variety of carriers as catalysts. The present inventors have developed a polymer incarcerated Lewis acid metal catalyst to make it possible to recover the catalyst by incarcerating a Lewis acid metal in a polymer to immobilize it on a carrier or to link it to a network while maintaining the functions of the Lewis acid metal catalyst (References 1 and 2).
Reference 1: International Publication WO2005/084802
Reference 2: J. Am. Chem. Soc. 2005, 127, 13096-13097

Problems to be Solved by the Invention

Although the polymer incarcerated Lewis acid metal catalyst that the present inventors developed functions well in aldol reactions, cyanolation reactions, allylation reactions, Michael reactions, Mannich reactions and the like, the use of the catalyst is limited in water-insoluble organic solvent and the catalyst cannot be used in water or water-soluble organic solvent. And a Scandium catalyst that can be used in water or water-soluble organic solvent without leaching of Scandium has not been known.

Therefore, the present invention is intended to provide a Scandium catalyst that can be used in water or water-soluble organic solvent with no leaching of Scandium.

Means to Solve the Problems

The inventors of the present invention composed a gold-polymer nanostructure-immobilized Scandium catalyst by reacting gold clusters having from about 1 to 50 nm of particle size with a disulfide having a sulfonic acid salt group and a vinyl group to incarcerate the gold clusters in the disulfide to form a gold-polymer nanostructure, making a Lewis acid metal compound of Scandium immobilized on the sulfonic acid salt group, and then polymerizing the vinyl group to form a polymer.

It was found that thus obtained catalyst can be used in water or water-soluble organic solvent and functions as a Scandium catalyst, and shows no leaching of Scandium.

That is, the present invention is a gold-polymer nanostructure-immobilized Scandium catalyst, which is formed by
(1) preparing, in liquid phase, a mixture comprising gold clusters with from 1 to 50 nm of diameter, disulfide monomer, sulfonic acid salt of disulfide and Lewis acid metal compound represented by $ScY_3$, wherein Y is a halogen atom, OAc, $OCOCF_3$, $ClO_4$, $SbF_6$, $PF_6$ or $OSO_2CF_3$, and
(2) polymerizing the mixture in the presence of a radical polymerization initiator, wherein the disulfide monomer is represented by the formula below:

$$CH_2=CH-R^1-S-S-R^1-CH=CH_2$$

wherein $R^1$ represents a divalent hydrocarbon, which may contain an ether bond, and the sulfonic acid salt of disulfide is represented by the formula below:

$$MO_3S-R^2-S-S-R^2-SO_3M$$

wherein $R^2$ represents a divalent hydrocarbon, which may contain an ether bond, and M represents an alkali metal.

The mixture may further comprise styrene monomer in the step of polymerization.

The present invention is also a use of the catalyst for aldol reactions, cyanolation reactions, allylation reactions, Michael reactions, Mannich reactions, Diels Alder reactions or Friedel Crafts reactions.

These reactions may be conducted in water, a water-soluble organic solvent or a mixture of these.

DETAILED DESCRIPTION OF THE INVENTION

Figure 1:
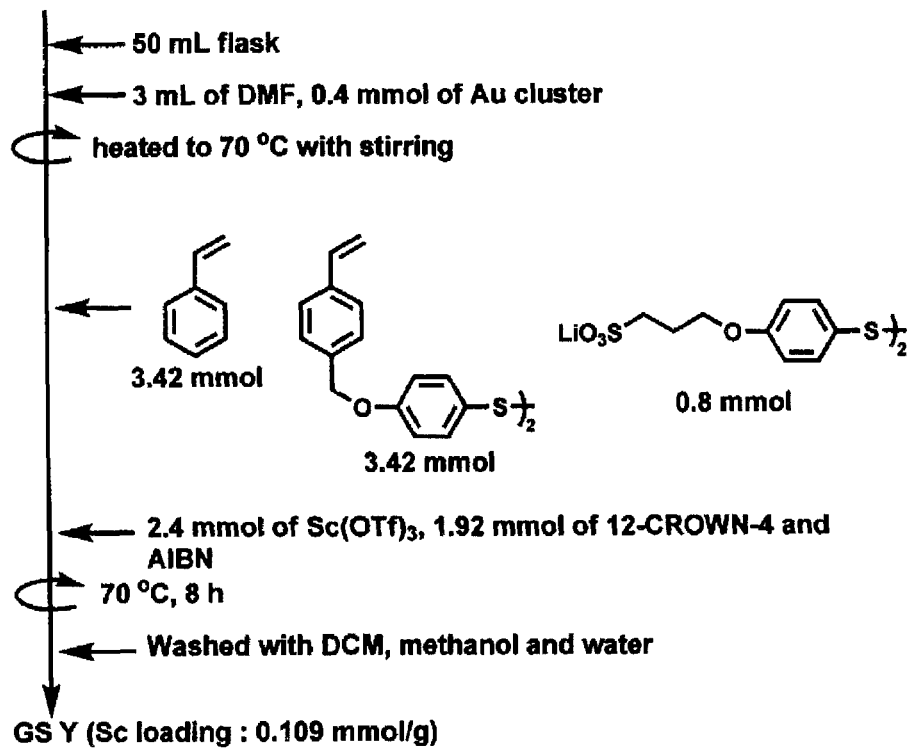
FIG. 1 shows the schematic diagram of the synthesis of the gold-polymer nanostructure-immobilized Scandium catalyst of Example 1.

The gold-polymer nanostructure-immobilized Scandium catalyst of the present invention is formed by preparing, in liquid phase, a mixture comprising gold clusters with from 1 to 50 nm, preferably from 1 to 10 nm, of diameter, disulfide monomer, sulfonic acid salt of disulfide and Lewis acid metal compound represented by $ScY_3$, wherein Y is described later, and polymerizing the mixture in the presence of a radical polymerization initiator.

The gold clusters used in the present invention is not particularly limited as long as the gold clusters are dispersed in normal solvent or organic materials as gold clusters with from 1 to 50 nm, preferably from 1 to 10 nm, of diameter. The method to prepare such gold clusters is well known (for example, Tsukuda et al. JACS, 2005, 127, 13464., Hutchison et al. J. Phys. Chem. B 2002, 106, 9979., Murray et al. JACS, 2005, 127, 8126. etc.).

The disulfide monomer used in the present invention is represented by the formula below:

$$CH_2=CH-R^1-S-S-R^1-CH=CH_2$$

wherein $R^1$ represents a divalent hydrocarbon, which may contain an ether bond (—O—). The divalent hydrocarbon is preferably alkylene group, arylene group or alkylene oxide, or a chain in which at least two of these are bonded in a block form, which may be linear or branched. The number of carbon atoms of the divalent hydrocarbon is preferably about 5 to 100. The alkylene group is, for example, —$(CH_2)_n$—, wherein n represents a number corresponding to the number of carbon atoms in the alkylene group, and the arylene group is, for example, phenylene group or naphthalene group. The alkylene oxide is, for example, —$(CH_2CH_2O)_n$— or —$(CH_2O)_n$—, wherein m represents a number corresponding to the number of carbon atoms in the alkylene oxide, or a mixture of these.

The sulfonic acid salt of disulfide used in the present invention is represented by the formula below:

$$MO_3S-R^2-S-S-R^2-SO_3M$$

wherein $R^2$ represents a divalent hydrocarbon chain, which may contain an ether bond, defined in the same manner as $R^1$.
M represents an alkali metal and is, for example, Li, Na, K, and the like.

The Lewis acid metal compound of Scandium used in the present invention is represented by $ScY_3$.

Y represents a halogen atom, OAc, OCOCF$_3$, ClO$_4$, SbF$_6$, PF$_6$ or OSO$_2$CF$_3$(OTf), preferably OTf.

The alkali metal M$^+$ of the sulfonic acid salt of disulfide is replaced with ScY$_2$+ of the Lewis acid metal compound in the solution, and the sulfonic acid salt of disulfide becomes a salt of Sc represented by the following formula.

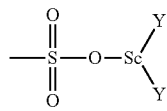

The disulfide bonded to gold clusters is polymerized, as described later, so that Sc metal is immobilized on the polymer and the leaching of Sc metal is eliminated.

When these are mixed in liquid phase, the disulfide monomer and the disulfide of the sulfonic acid salt of disulfide predominantly bind to the gold clusters as Au—S bond, which results in a morphology in which the gold clusters are incarcerated by the disulfide monomer and the sulfonic acid salt of disulfide.

A styrene monomer may be added to the mixture.

The solvent used in the present invention is not limited, and a polar solvent, such as THF, dioxane, acetone, DMF, NMP, methanol, ethanol, butanol, amylalcohol and the like and a non-polar solvent, such as toluene, cyclohexane, dichloromethane, chloroform, hexane, heptane, octane and the like may be used.

The content of the disulfide monomer in the solution is from 0.5 to 4 M, preferably from 1 to 2 M. The amount of sulfonic acid salt of the disulfide is from 0.1 to 10 mol, preferably from 0.5 to 2 mol, per 1 mol of the disulfide monomer. The amount of Lewis acid metal compound of Scandium is from 1 to 10 mol, preferably from 1.5 to 3 mol, per 1 mol of the disulfide monomer. The amount of styrene monomer is from 0 to 50 mol, preferably from 1 to 9 mol, per 1 mol of the disulfide monomer.

In this way, the gold clusters are incarcerated by the disulfide monomer and the sulfonic acid salt of disulfide and the trivalent Scandium is immobilized to form a micellar mixture, which may further optionally contain styrene monomer.

This micellar mixture may be polymerized by crosslinking the vinyl group of the disulfide monomer and the styrene monomer that is optionally mixed.

The polymerization reaction may be conducted according to previously well known methods by using a radical polymerization catalyst such as a peroxide, an azo compound or the like.

The temperature of the polymerization is ordinarily from about 50 to about 160 degree C., preferably from about 60 to about 120 degree C.

The reaction time over which the heated polymerization reaction is ordinarily from 0.1 hour to one hundred hours, preferably from one to ten hours.

Thus obtained gold-polymer nanostructure-immobilized Scandium catalyst can be used in aldol reactions, cyanolation reactions, allylation reactions, Michael reactions, Mannich reactions, Diels Alder reactions, Friedel Crafts reactions and the like, and shows a very high activity.

The catalyst of the present invention can used in any type of solvent, and especially can be used in water, a water-soluble organic solvent or a mixture of these. In particular, the catalyst is characterized in that there is no leaching of Scandium metal.

As the water-soluble organic solvent, alcohols such as methanol, ketones such as acetone, acetonitrile and THF and the like may be cited.

EXAMPLES

The present invention is illustrated in the Examples below, but it is not the intention of the Examples to restrict the present invention.

$^1$H NMR and $^{12}$C NMR are measured by using JEOL JNM-ECX-400, JNM-ECX-500 or JNM-ECX-600 with CDCl$_3$ as a solvent and tetramethylsilane ($\delta$=0, $^1$H NMR) or CDCl$_3$ ($\delta$=77.0, $^{13}$C NMR) as an internal standard substance.

High-resolution mass spectrum (HR-ESIMS) was measured by using BRUKER DALTONICS BioTOF II mass spectrometer and JEOL JMS-T100TD AccuTOF TLC.

Inductively Coupled Plasma (ICP) analysis was measured by using Shimadzu ICPS-7510. Silica gel 60 (Merck) was used for column chromatography and Wakogel B-5F (Wako Pure Chemical Industries, Ltd.) was used for thin-layer chromatography for adjustment.

Production Example 1

4-4'-disulfanediyldiphenol was synthesized in this Production Example.

25.0 g of para-hydroxy thiophenol (Wako Pure Chemical Industries, Ltd.) was dissolved in 100 ml of dimethyl sulfoxide (Kanto Chemical Co., Ltd.) at 0 degree C. The reaction solution was stirred for 24 hours at 65 degree C. and cooled to 0 degree C. after the completion of the reaction. Then the mixture was diluted with 100 ml of diethyl ether (Wako Pure Chemical Industries, Ltd.). Water was added to this solution and the aqueous phase was extracted with 50 ml of diethyl ether three times. Then the organic phase was dried by using sodium sulfate (Wako Pure Chemical Industries, Ltd.) and recrystallized in chloroform (Wako Pure Chemical Industries, Ltd.). 4,4'-disulfanediyldiphenol was obtained (23.8 g, yield 96%).

Analysis results of the product are shown below:

$^1$H NMR (DMSO-d$_6$) $\delta$ 6.75-6.77 (d, J=8.6 Hz, 4H), 7.26-7.28 (d, J=8.6 Hz, 4H) 9.86 (br s, 2H); $^{13}$C NMR (DMSO-d$_6$) $\delta$ 116.4, 125.1, 133.1, 158.3; HIMS (m/z) calcd. for C$_{12}$H$_{10}$O$_2$S$_2$ (MH+): 250.01135. found: 250.01218.

Production Example 2

1,2-bis(4-(4-vinylbenzyloxy)phenyl)disulfane was synthesized in this Production Example.

30.2 g of 4,4'-disulfanediyldiphenol obtained in the Production Example 1 and 50 g of potassium carbonate (Wako Pure Chemical Industries Co., Ltd.) were dissolved in 200 ml of DMF (special grade, Tokyo Chemical Industry Co., Ltd.) at room temperature. Then 40.5 g of 1-chloromethyl-4-vinylbenzene (Aldrich, 40.5 g) was added to the solution and heated to 85 degree C. The reaction solution was stirred for 24 hours. Then the solution was cooled to 0 degree C. and was diluted by adding 100 ml of dichloromethane (Kanto Chemical products Co., Ltd.) and was quenched with water. The aqueous phase was extracted with 100 ml of dichloromethane and the combined organic phase was dried over sodium sulfate. Then the organic solvent was evaporated and the residue was washed with hexane and 1,2-bis(4-(4-vinylbenzyloxy)phenyl)disulfane was obtained (50.2 g, yield 86%).

Analysis results of the product are shown below:
$^1$H NMR (CDCl$_3$) δ 5.03 (s, 41-1), 5.25-5.27 (d, J=10.9 Hz, 2H) 5.75-5.78 (d, J=17.8 Hz, 2H), 6.69-6.75 (dd, J=6.3 Hz, 11.5 Hz, 11.5 Hz, 2H), 6.88-6.90 (d, J=9.2 Hz, 4H), 7.36-7.44 (m, 12H); $^{13}$C NMR (CDCl$_3$) δ 69.8, 114.2, 115.5, 126.4, 127.7, 128.7, 132.4, 136.0, 136.3; DART-MS (m/z) calcd. for C$_{30}$H$_{26}$O$_2$S$_2$ (MH$^+$): 482.13742. found: 482.13608.

Production Example 3

Lithium 3'-(4,4'-disulfanediylbis(4,1-phenylene)bis(oxy))dipropane-1-sulfonate was synthesized in this Production Example.

6.47 g of 1,2-bis(4-(4-vinylbenzyloxy)phenyl)disulfane obtained in the Production Example 1 was dissolved in 100 ml of ethanol (Wako Pure Chemical Industries, Ltd.) and was cooled to 0 degree C. Then 2.58 g of lithium hydroxide (special grade, Tokyo Chemical Industry Co., Ltd.) was added to the solution. The mixture was warmed to room temperature and was stirred for 1 hour. Then the reaction solution was cooled to 0 degree C. and 7.89 g of sultone (Wako Pure Chemical Industries, Ltd.) was added. The reaction solution was warmed to room temperature and was stirred for 24 hours.

Then the solid formed after the completion of the reaction was washed with 100 ml of ethanol (Wako Pure Chemical Industries Co., Ltd.) and lithium 3'-(4,4'-disulfanediylbis(4,1-phenylene)bis(oxy))dipropanme-1-sulfonate was obtained (11.6 g, yield 85%).

Analysis results of the product are shown below:
$^1$H NMR (D$_2$O) δ 2.01-2.04 (m, 4H), 2.89-2.91 (t, J=7.6 Hz, 8.2 Hz, 4H), 3.94-3.96 (t, J=6.2 Hz, 6.9 Hz, 4H), 6.75-6.77 (d, J=8.3, 4H), 7.26-7.27 (d, J=8.9 Hz, 4H); $^{13}$C NMR (D$_2$O) δ 24.9, 48.5, 67.2, 116.0, 128.6, 132.5, 158.9.

Production Example 4

Gold cluster was prepared by the method described in a literature (JACS, 2005, 127, 13464-13465) in this Production Example.

76 mg of sodium borohydride (NaBH3, Wako Pure Chemical Industries Co., Ltd.) was added to 55 ml of ethanol solution of 1.0 g of chlorotriphenylphosphine (AuClPPh3, Wako Pure Chemical Industries Co., Ltd.) for over 15 minutes. After stirring for 2 hours at room temperature, this mixture was poured into 1 L of hexane and was stirred for 20 hours. Brown colored solid was obtained by filtering the mixture with a membrane filter. Then the solid obtained on the membrane filter was washed with dichloromethane/hexane (1:1, 4×15 ml) and dichloromethane/hexane (3:1, 10 ml).

The solid remained on the membrane filter was dissolved in 100 ml of hexane and dichloromethane was evaporated. Then 382 mg of gold clusters was obtained.

Example 1

Figure 2:
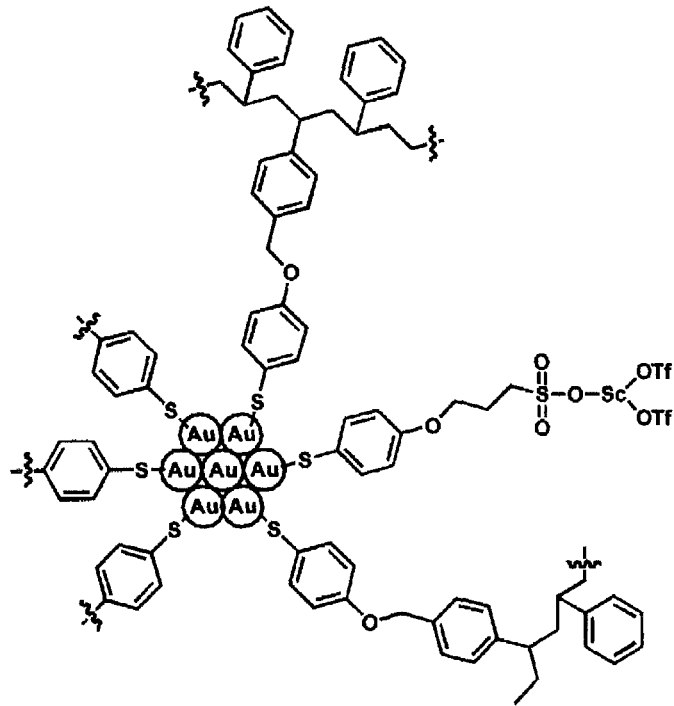
FIG. 2 shows the structure of the gold-polymer nanostructure-immobilized Scandium catalyst of Example 1.

A gold-polymer nano structure-immobilized Scandium catalyst was synthesized by using the materials obtained in the Production Examples 2-4. The schematic diagram of the synthesis is shown in FIG. 1 and the structure of the synthesized catalyst is shown in FIG. 2.

The gold clusters (0.4 mmole as Au) prepared in the Production Example 4 was dissolved in 3 ml of DMF (Wako Pure Chemical Industries Co., Ltd.) and was heated to 70 degree C. Then 3.42 mmole of styrene (Tokyo Chemical Industry Co., Ltd.), 43 mmole of 1,2-bis(4-(4-vinylbenzyloxy)phenyl)disulfane prepared in the Production Example 2, 3.42 mmole of lithium 3'-(4,4'-disulfanediylbis(4,1-phenylene)bis(oxy))dipropanme-1-sulfonate prepared in the Production Example 3, 2.4 mmole of Scandium triflate (Sc(OTf)$_3$, Wako Pure Chemical Industries Co., Ltd.), 1.92 mmole of 12-crown-4-ether (Tokyo Chemical Industry Co., Ltd.) and 0.034 mmole of AIBN (azobisisobutyronitrile, Wako Pure Chemical Industries, Ltd.) were added and heated for 8 hours at 70 degree C. Then a solid was formed and the solid was washed with 50 ml of dichloromethane, 50 ml of methanol (Wako Pure Chemical Industries, Ltd.) and water and a Scandium catalyst was obtained (hereinafter referred to as "GY catalyst"). The content of metals in the Scandium catalyst were Sc 0.0804 mmole/g, Au 0.132 mmole/g and Li. 0.0303 mmole/g, respectively.

Example 2

A Scandium catalyst (hereinafter referred to as "GS X catalyst") was prepared in the same manner as described in Example 1 with the exception that a mixed solvent with 2:1 volume ratio of chloroform and water was used for the solvent DMF. The content of metals in the Scandium catalyst were Sc 0.0500 mmole/g, Au 0.100 mmole/g and Li. 0.0180 mmole/g, respectively.

Example 3

In this Example, a hydroxymethylated compound was synthesized from formaldehyde and silicon enolate by using the GS Y catalyst obtained in Example 1, according to the formula below.

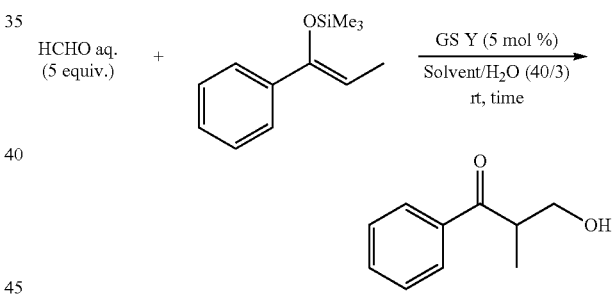

GS Y catalyst (0.02 mmole as Sc) was added to 2 ml of acetonitrile (Wako Pure Chemical Industries Co., Ltd.), then 150 μl of 37% aqueous formaldehyde solution (Wako Pure Chemical Industries Co., Ltd.) and 0.4 mmole of silyl enol ether (Wako Pure Chemical Industries, Ltd.) were added. The mixture was stirred under an argon atmosphere at room temperature for 5 hours. The CS Y catalyst was removed by filtration, the solvent was evaporated and the residue was purified by thin-layer chromatography (pTLC) and a hydroxymethylated compound (3-hydroxy-2-methyl-1-phenylpropan-1-one) was obtained.

The same reaction was conducted in the same manner as described above with the exception of changing the solvent to THF (Wako Pure Chemical Industries, Ltd., dehydrated). And the catalyst was reused.

Analysis results of the product are shown below:
$^1$H NMR (CDCl$_3$) δ 1.23-1.25 (d, J=7.4 Hz, 3H), 2.28 (br s, 1H), 3.67 (m, 1H), 3.83 (m, 1H), 3.93 (m, 1H), 7.46-7.61 (m, 3H), 7.95-7.98 (m, 2H); $^{13}$C NMR (CDCl$_3$) δ 14.5, 42.9, 64.5, 128.4, 128.7, 133.3, 136.1, 204.4.

And the result of the reaction is shown in the table below:

TABLE 1

| Entry | Solvent | Time | Run | Yield (%) |
|---|---|---|---|---|
| 1 | MeCN | 5 h | 1 | 72 |
| 2 | | | 2 | 74 |
| 3 | | | 1 | 80 |
| 4 | THF | 2 days | 2 | 73 |
| 5 | | | 3 | 65 |
| 6 | THF | 5 h | 1 | 53 |

The GS Y catalyst of the present invention functioned well in the hydroxymethylation reaction using the formaldehyde aqueous solution of the silyl enol ether. In spite of using the water solvent, leaching of Scandium was not observed in the ICP analysis. It was also shown that the catalyst can be recovered and reused.

Example 4

In this Example, the same reaction was conducted in the same manner as Example 3 with the exception of using the GS X catalyst obtained in Example 2 instead of the GS Y catalyst, using THF solvent, and the reaction time being two days. As a result, the same hydroxymethylated compound (3-hydroxy-2-methyl-1-phenylpropan-1-one) as in Example 3 was obtained. The result of the reaction is shown in the table below:

TABLE 2

| Entry | Catalyst | Reuse | Yield (%) | Leaching (%) |
|---|---|---|---|---|
| 1 | GS X | 1 | 71 | ND |
| 2 | | 2 | 76 | ND |

The GS X catalyst showed almost the same performance as the GS Y catalyst. Leaching of Scandium was not observed in the ICP analysis. The catalyst can be recovered and reused.

Comparative Example 1

In this Comparative Example, the same reaction was conducted in the same manner as Example 3 with the exception of using Scandium oxide ($Sc_2O_3$, Wako Pure Chemical Industries, Ltd., special grade) or Scandium chloride ($ScCl_3$, Wako Pure Chemical Industries, Ltd., special grade) with the amount of Scandium being adjusted to 0.02 mmole instead of the GS Y catalyst. As a result, the yield of the hydroxymethylated compound (3-hydroxy-2-methyl-1-phenylpropan-1-one) were 0% in the case of using Scandium oxide and 21% in the case of using Scandium chloride, respectively.

Example 5

In this Example, Julolidine derivatives were synthesized by using the GS Y catalyst obtained in Example 1, according to the formula below.

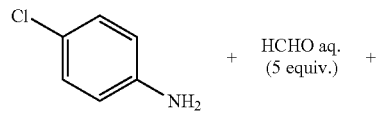

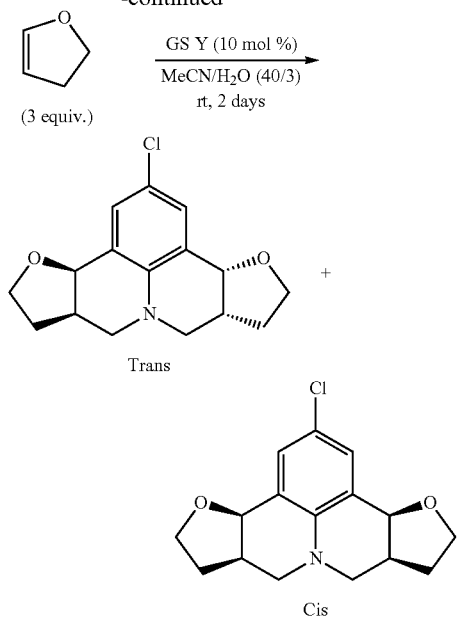

GS Y catalyst (0.02 mmole as Sc) was added to 2 ml of acetonitrile (Wako Pure Chemical Industries Co., Ltd.), then 51.0 mg of para-chloro-aniline (Wako Pure Chemical Industries Co., Ltd.) and 90.4 μl of 2,3-dihydrofuran (Tokyo Chemical Industry Co., Ltd.) were added. The mixture was stirred under an argon atmosphere at room temperature for 48 hours. The CS Y catalyst was removed by filtration, the solvent was evaporated and the residue was purified by thin-layer chromatography (pTLC) and Julolidine derivatives were obtained (overall yield 98%, Trans form 54%, Cis form 44%).

Leaching of Scandium was not observed in the ICP analysis. Analysis results of the product are shown below:

Julolidine derivative Trans form:

$^1$H NMR ($CDCl_3$) δ 1.89-1.92 (m, 2H), 2.15-2.18 (m, 2H), 2.60 (m, 2H), 2.80-2.83 (m, 2H), 2.97-3.00 (m, 2H), 3.77-3.82 (m, 2H), 3.86-3.90 (m, 2H), 4.68-4.70 (d, J=6.3 Hz, 2H), 7.22 (s, 2H); $^{13}$C NMR ($CDCl_3$) δ 24.8, 29.3, 36.1, 51.1, 65.9, 74.5, 123.0, 123.9, 130.1, 142.3; DART-MS (m/z) calcd. for $C_{16}H_{18}NO_2Cl$ ($MH^+$): 291.10261. found: 291.10343. CCDC 762699.

Julolidine derivative Cis form:

$^1$H NMR ($CDCl_3$) δ 1.70-1.74 (m, 2H), 2.24-2.29 (m, 2H), 2.50 (m, 2H), 2.59 (m, 2H), 2.93-2.96 (m, 2H), 3.79-3.84 (m, 2H), 3.93-3.98 (m, 2H), 4.47-4.48 (d, J=4.6, 2H), 7.28 (s, 2H); $^{13}$C NMR ($CDCl_3$) δ 30.0, 30.9, 35.4, 51.0, 66.0, 123.6, 127.9, 132.3, 142.8; DART-MS (m/z) calcd. for $C_{16}H_{15}NO_2Cl$ ($MH^+$): 291.10261. found: 291.10343. CCDC 762698.

Comparative Example 2

In this Comparative Example, the same reaction was conducted in the same manner as Example 5 with the exception of using Scandium triflate ($Sc(OTf)_3$, Wako Pure Chemical Industries, Ltd.) instead of the GS Y catalyst. As a result, the same Julolidine derivatives as Example 5 were obtained, but the yield were lower (overall yield 71%, Trans form 35%, Cis form 35%).

What is claimed is:

1. A gold-polymer nanostructure-immobilized Scandium catalyst, which is formed by
   (1) preparing, in liquid phase, a mixture comprising gold clusters having particle diameters of from 1 to 50 nm, a disulfide monomer, a sulfonic acid salt of a disulfide, and a Lewis acid metal compound represented by $ScY_3$, wherein Y is a halogen atom, OAc, $OCOCF_3$, $ClO_4$, $SbF_6$, $PF_6$ or $OSO_2CF_3$, and
   (2) polymerizing the mixture in the presence of a radical polymerization initiator,
   wherein the disulfide monomer is represented by the formula below:

$CH_2\!=\!CH\!-\!R^1\!-\!S\!-\!S\!-\!R^1\!-\!CH\!=\!CH_2$, wherein $R^1$ represents a divalent hydrocarbon, which may contain an ether bond, and wherein the sulfonic acid salt of the disulfide is represented by the formula below:

$MO_3S\!-\!R^2\!-\!S\!-\!S\!-\!R^2\!-\!SO_3M$, wherein $R^2$ represents a divalent hydrocarbon, which may contain an ether bond, and M represents an alkali metal.

2. The catalyst of claim 1 wherein the mixture further comprises styrene monomer in the step of polymerization.

3. A method of performing a chemical reaction comprising contacting the catalyst of claim 1 with one or more reagents for performing aldol reactions, cyanolation reactions, allylation reactions, Michael reactions, Mannich reactions, Diels Alder reactions or Friedel Crafts reactions.

4. The method of claim 3 wherein the reaction is conducted in water, a water-soluble organic solvent or a mixture of these.

5. A method of performing a chemical reaction comprising contacting the catalyst of claim 2 with one or more reagents for performing aldol reactions, cyanolation reactions, allylation reactions, Michael reactions, Mannich reactions, Diels Alder reactions or Friedel Crafts reactions.

6. The method of claim 5 wherein the reaction is conducted in water, a water-soluble organic solvent or a mixture of these.

* * * * *